US008746046B2

(12) United States Patent
Zanetti et al.

(10) Patent No.: US 8,746,046 B2
(45) Date of Patent: Jun. 10, 2014

(54) METHOD FOR THE ESTIMATION OF OIL VISCOSITY IN AN INTERNAL COMBUSTION ENGINE

(75) Inventors: Igor Zanetti, Verrayes (IT); Stefano Cassani, Turin (IT)

(73) Assignee: GM Global Technology Operations LLC, Detroit, MI (US)

( * ) Notice: Subject to any disclaimer, the term of this patent is extended or adjusted under 35 U.S.C. 154(b) by 468 days.

(21) Appl. No.: 13/102,687

(22) Filed: May 6, 2011

(65) Prior Publication Data

US 2011/0285537 A1 Nov. 24, 2011

(30) Foreign Application Priority Data

May 21, 2010 (GB) .................................. 1008497.8

(51) Int. Cl.
*G01N 33/26* (2006.01)

(52) U.S. Cl.
USPC .......................... 73/53.05; 73/54.01; 340/603

(58) Field of Classification Search
USPC ........................................................ 73/53.05
See application file for complete search history.

(56) References Cited

U.S. PATENT DOCUMENTS

| | | | | |
|---|---|---|---|---|
| 6,889,653 | B2 * | 5/2005 | Kang et al. | 123/395 |
| 2006/0283421 | A1 | 12/2006 | Chiba et al. | |
| 2008/0163678 | A1 * | 7/2008 | Snider et al. | 73/53.05 |

FOREIGN PATENT DOCUMENTS

| | | |
|---|---|---|
| JP | 2003120390 A | 4/2003 |

OTHER PUBLICATIONS

British Patent Office, British Search Report for British Application No. 1008497.8, dated Sep. 6, 2010.

* cited by examiner

*Primary Examiner* — Hezron E Williams
*Assistant Examiner* — Mark A Shabman
(74) *Attorney, Agent, or Firm* — Ingrassia Fisher & Lorenz, P.C.

(57) ABSTRACT

A method for the estimation of oil viscosity in an internal combustion engine, the engine subjected to fuel post injections to activate Particulate Filter regeneration processes and to fuel hydrocarbons (HC) evaporation events affecting said oil viscosity. The method includes, but is not limited to determining if the particulate filter is subjected to a regeneration process and, in the affirmative case, calculating an oil viscosity decrease during said Particulate Filter regeneration process as a function of an oil dilution rate, and calculating an oil viscosity increase after said regeneration process as a function of an Hydrocarbon (HC) evaporation rate and of a time during which fuel Hydrocarbon evaporation takes place, where said evaporation time is determined as a function of a time spent in evaporating fuel Hydrocarbon from engine oil in a previous fuel hydrocarbons evaporation event.

12 Claims, 4 Drawing Sheets

METHOD FOR THE ESTIMATION OF OIL VISCOSITY IN AN INTERNAL COMBUSTION ENGINE

CROSS-REFERENCE TO RELATED APPLICATION

This application claims priority to British Patent Application No. 1008497.8, filed May 21, 2010, which is incorporated herein by reference in its entirety.

TECHNICAL FIELD

The technical field relates to a method for the estimation of oil viscosity in an Internal Combustion Engine (ICE).

BACKGROUND

In order to comply with present and future environmental legislation, current vehicles are provided with anti-Particulate Filters which are devices located in the exhaust line of the engine designed to trap the soot in order to clean the exhaust gas. Electronics systems managing the engine are capable to recognize when the filter is full; at this time they command a so-called regeneration process: this is, in principle, a process to empty out the filter based on soot auto-combustion inside the filter itself. Filter regeneration is achieved by an exhaust gas temperature increase (up to 630° C. or more) for a short time (around 10 minutes).

In order to achieve the needed temperature for regenerating the anti-Particulate Filter, so called post injections are employed; these are fuel injections that are activated during the regeneration process and that occur after the Top Dead Center (TDC) of the piston. These post injections, since they occur very far from the TDC, represent a contribution to HydroCarbon (HC) exhaust content. Due to these phenomena, fuel from post injections more likely hits and wets the walls of the combustion chamber and is adsorbed to the oil, causing a decrease of the oil viscosity.

On the contrary, during normal operation of the engine, some of the fuel HydroCarbons (HC) previously adsorbed inside the oil evaporate, causing an increase of oil viscosity. The intensity of both these phenomena depends on the engine and vehicle working conditions, which can be summarized as vehicle Mission Profiles. Also, these phenomena have an impact on engine oil life and contribute to determine the necessity of oil change.

Excessively low viscosity of the oil can lead to engine damage. Also, an inaccurate estimation of oil viscosity can lead to unnecessary high rate of oil change events.

Current methods used for the estimation of oil viscosity only consider a constant oil dilution rate and a constant HydroCarbons (HC) evaporation rate in every working condition of the engine. Also, these methods do not consider the limitation of the evaporation phase that may occur due to a saturation in the physical phenomena. Finally these methods do not take into account the history of the oil in the engine that is relevant especially after a certain number of particulate filter regeneration events. Due to these factors, current methods exhibit a behavior that does not appear sufficiently accurate.

At least one object is obtain an improvement in the estimation of engine oil viscosity that provides a more accurate oil viscosity information for a variety of uses. At least a further object is to use such improved estimation to greatly reduce the risk of engine failure or damage due to insufficient oil viscosity. At least another object is to provide such accurate oil viscosity information without using complex devices and by taking advantage from the computational capabilities of the Electronic Control Unit (ECU) of the vehicle. Yet another object of the present disclosure is to meet these goals by means of a rather simple, rational and inexpensive solution. In addition, other objects, desirable features and characteristics will become apparent from the subsequent summary and detailed description, and the appended claims, taken in conjunction with the accompanying drawings and this background.

SUMMARY

An embodiment provides for a method for the estimation of oil viscosity in an Internal Combustion Engine, said engine being subjected to fuel post injections to activate Particulate Filter regeneration processes and to fuel hydrocarbons (HC) evaporation events affecting said oil viscosity, said method comprising determining if the Particulate Filter is subjected to a regeneration process and, in the affirmative case, calculating an oil viscosity decrease during said Particulate Filter regeneration process as a function of an oil dilution rate, calculating an oil viscosity increase after said regeneration process as a function of an Hydrocarbon (HC) evaporation rate and of a time during which fuel Hydrocarbon evaporation takes place, where said evaporation time is determined as a function of a time spent in evaporating fuel Hydrocarbon from engine oil in a previous fuel hydrocarbons evaporation event. An advantage of the above method is that it allows to reliably estimate oil viscosity during the use of the vehicle by calculating the oil viscosity in real time, while the engine is running, taking into consideration the oil dilution and HC evaporation processes during the whole vehicle lifetime.

According to an embodiment of the method, in which the oil viscosity value is incremented until the time spent in evaporating fuel Hydrocarbon from engine oil reaches a setpoint value. An advantage of this embodiment is that it allows to estimate the behavior of hydrocarbon evaporation affecting oil viscosity presetting a suitable setpoint corresponding to an evaporation saturation phenomenon.

According to a further embodiment of the method, different setpoint values for the time spent in evaporating fuel Hydrocarbon are preset for each mission profile of the engine. Advantageously this embodiment allows to take into account the different evaporation phenomena that occurs as a consequence of different mission profiles.

According to another embodiment of the method, a different oil dilution rate is set for each regeneration process on the basis of the specific mission profile in which the engine is operating. This embodiment allows advantageously to take into account the different oil dilution rate that occurs as a consequence of different mission profiles.

According to still another embodiment of the method a different Hydrocarbon (HC) evaporation rate is set for each Hydrocarbon (HC) evaporation following a regeneration process on the basis of the mission profile in which the engine is operating. An advantage of this embodiment is that it allows to take into account the evaporation rate of fuel affecting oil viscosity as a function of different mission profiles.

According to still another embodiment of the invention it is provided a method for operating an Internal Combustion Engine, said engine being subjected to fuel post injections to activate Particulate Filter regeneration processes and to fuel hydrocarbons (HC) evaporation events affecting said oil viscosity, said method comprising determining if the Particulate Filter is subjected to a regeneration process and, in the affirmative case, calculating an oil viscosity decrease during said Particulate Filter regeneration process as a function of an oil dilution rate, calculating an oil viscosity increase after said regeneration process as a function of an Hydrocarbon (HC) evaporation rate and of a time during which fuel Hydrocarbon evaporation takes place, where said evaporation time is determined as a function of a time spent in evaporating fuel Hydrocarbon from engine oil in a previous fuel hydrocarbons evaporation event, and generating a warning signal if the oil viscosity value drops below a first predetermined minimum threshold value. An advantage of this embodiment is that it helps in avoiding the risk of engine damage due to overestimated oil life. Furthermore, it reduces the number of oil changes, since an accurate estimate can lead to improved mileage between subsequent oil changes, thus also improving customer satisfaction.

According to another embodiment of the invention, if the oil viscosity value drops below the first predetermined minimum threshold value or below a second predetermined minimum threshold value lower than the first predetermined minimum threshold value, the engine is operated in an operating mode in which the torque generated by the engine may not exceed a preset maximum threshold torque value. An advantage of this embodiment is that it helps in avoiding or at least reducing the risk of engine damage due to overestimated oil life in case the driver does not take immediate action after the warning signal.

The method can be carried out with the help of a computer program comprising a program-code for carrying out all the steps of the method described above, and in the form of computer program product comprising the computer program. The computer program product can be embodied as a control apparatus for an internal combustion engine, comprising an Electronic Control Unit (ECU), a data carrier associated to the ECU, and the computer program stored in a data carrier, so that the control apparatus defines the embodiments described in the same way as the method. In this case, when the control apparatus executes the computer program all the steps of the method described above are carried out.

The method can be also embodied as an electromagnetic signal, said signal being modulated to carry a sequence of data bits which represents a computer program to carry out all steps of the method. A still further embodiment provides an internal combustion engine specially arranged for carrying out the method claimed.

BRIEF DESCRIPTION OF THE DRAWINGS

The present invention will hereinafter be described in conjunction with the following drawing figures, wherein like numerals denote like elements, and.

DETAILED DESCRIPTION OF THE DRAWINGS

The following detailed description is merely exemplary in nature and is not intended to limit application and uses. Furthermore, there is no intention to be bound by any theory presented in the preceding background or summary or the following detailed description.

Figure 1:
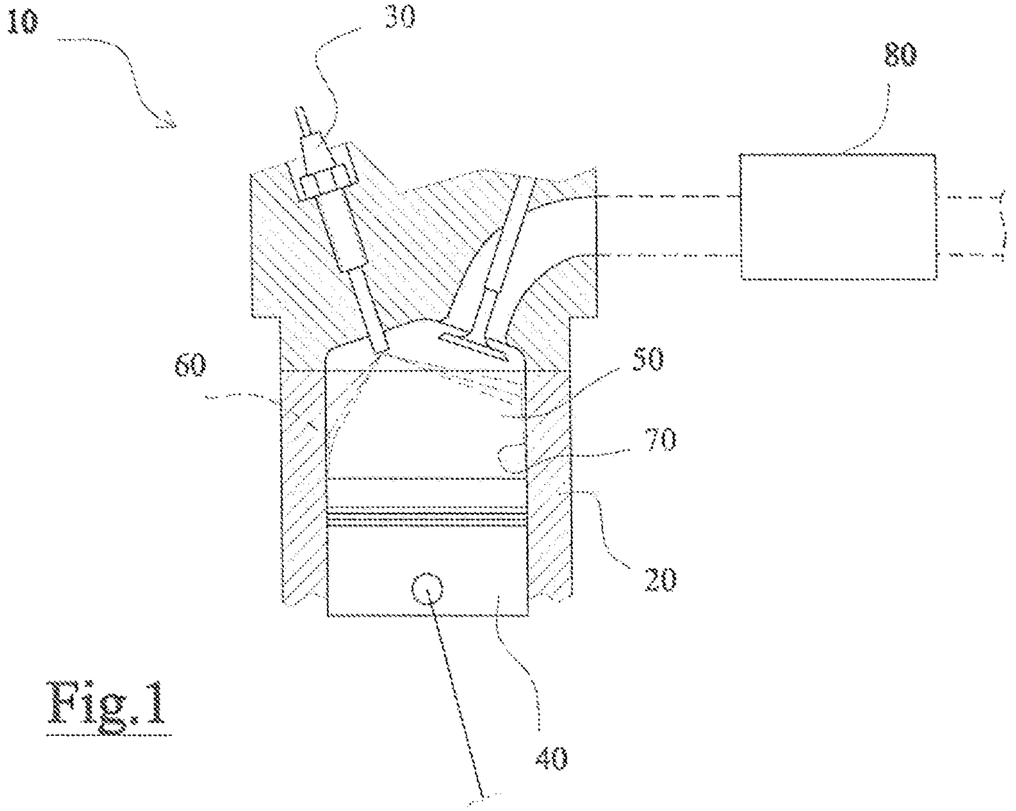
FIG. 1 is a schematic representation of a cylinder-piston assembly of an Internal Combustion Engine (ICE) in a post-injection mode.

In FIG. 1 a cylinder 20 and piston 40 group belonging to an Internal Combustion Engine (ICE) 10 is depicted during a post-injection event related to a particulate filter 80 regeneration process, and in which a fuel injector 30 post-injects a quantity of post injection fuel 60 into a combustion chamber 50.

During a particulate filter 80 regeneration process, post injection fuel hits and wets the walls 70 of the combustion chamber 50 and is adsorbed to the oil veil, causing a decrease of the oil viscosity. During normal operation of the engine that follows a regeneration process, some of the fuel hydrocarbons previously adsorbed into the oil evaporate, causing an increase of oil viscosity.

Figure 3:
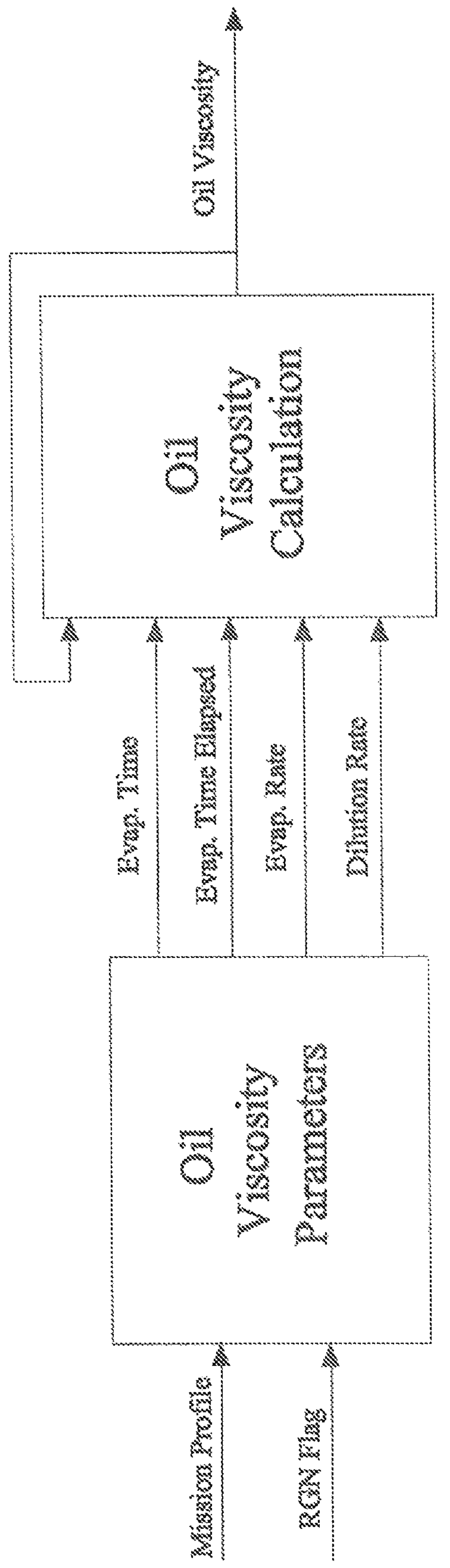
FIG. 3 is a schematic illustration of the main variables for the oil viscosity estimation according to an embodiment.

FIG. 3 is a schematic illustration of the variables that intervene in the oil viscosity estimation method, according to an embodiment of the present invention. In particular, the method employs variables belonging to two main blocks, a first block that takes into account operating conditions affecting oil viscosity, namely the specific mission profile that the vehicle is subjected to, and the fact that the engine is performing or not a regeneration process. A specific example of a regeneration process considered is a Diesel Particulate Filter (DPF) regeneration process.

A second block depicted in FIG. 3 performs an oil viscosity calculation as a function of oil Evaporation Rate, oil Evaporation Time and oil Evaporation Time Elapsed during a previous evaporation event. The model takes also into account an oil Dilution Rate, which is used for viscosity reduction estimation during Particulate filter regeneration phases.

According to an embodiment of the method for the estimation of oil viscosity in a Internal Combustion Engine (ICE), it is provided for a determination of the presence or not of a regeneration process. In this case a RGN_flag variable, or similar, is set accordingly.

In general the method considers also different mission profiles that may be employed during use of the vehicle and that affects engine operating conditions and oil viscosity related phenomena. The mission profile definition herein employed involves one engine operating area for each mission profile and, eventually, additional parameters based for example on vehicle speed, gear and engine coolant temperature.

An example of mission profiles data that may be employed in the present method is given in the following table 1:

TABLE 1

| | Mission Profile | Engine operating conditions |
|---|---|---|
| 1 | TRANSIENT | N = 2000 rpm<br>BMEP = 18 bar |
| 2 | HIGHWAY<br>HIGH | N = 3500 rpm<br>BMEP = 8 bar |
| 3 | HIGHWAY<br>LOW | N = 2500 rpm<br>BMEP = 8 bar |
| 4 | EXTRA-<br>URBAN | N = 2000 rpm<br>BMEP = 5 bar |

TABLE 1-continued

| | Mission Profile | Engine operating conditions |
|---|---|---|
| 5 | URBAN HIGH | N = 1500 rpm<br>BMEP = 2 bar |
| 6 | URBAN LOW | LOW IDLE (850 rpm) |

Where BMEP indicates Brake Mean Effective Pressure. The mission profiles above are merely exemplary and other mission profiles may be employed depending on the circumstances without departing from the inventive concepts herein disclosed.

A fuel hydrocarbon (HC) evaporation event follows a particulate filter regeneration process and such evaporation affects oil viscosity and, in particular, increments such viscosity. Such evaporation event takes place for a measurable amount of time and the evaporated fuel quantity is a non-linear function of time that, at the end of a specific evaporation event, reaches a saturation value after which no further evaporation substantially occurs. The evaporated fuel quantity is also a function of the specific mission profile of the vehicle, whereby different mission profiles give rise to different evaporated fuel quantity functions over time.

In order to approximate the complex behavior of oil viscosity change over time, the present method presets an Evaporation Rate value for each mission profile and an Evaporation Time variable that indicates the time during which fuel hydrocarbons (HC) evaporation takes place. The multiplication of the Evaporation Rate value with the Evaporation Time variable allows to estimate the fuel hydrocarbon (HC) evaporated quantity and, consequently, the oil viscosity increase during the specific evaporation event, this latter quantity being correlated with the fuel evaporation.

Since oil viscosity increase is affected by such evaporated fuel quantity, it is also necessary to take into account the history of the regeneration processes and, after the end of these processes, of the relative subsequent evaporation events.

Both changes in mission profile and succession of regeneration processes followed by periods of normal engine operation interact in a real case and the present method takes also into account this interaction. Moreover, the fuel diluted in the oil during a regeneration event is composed by different kinds of hydrocarbons that are evaporable differently in different mission profiles. Each mission profile has thus the capability to evaporate mainly only some kinds of hydrocarbons with a different rate. This fact gives a further reason for the fact that dependency on the specific mission profile is taken into account in the present estimation method as detailed hereafter.

A variable Evaporation Time Elapsed is employed that indicates time spent evaporating fuel hydrocarbons (HC) from the engine oil in a previous evaporation event; this variable is used for estimating oil viscosity change in normal mode of operation of the engine. The variable Evaporation Time Elapsed has also a setpoint that takes into account the time needed for a specific evaporation event to be completed, or in other words to reach saturation, and that therefore, until a new regeneration processes is started and has come to its end, no further evaporation occurs. In these cases, having reached its setpoint, the variable oil viscosity is not incremented further.

As a general rule, the Evaporation Time Elapsed variable has different setpoints, each one for a different mission profile. The variable Evaporation Time depends on the specific Mission Profile and it is updated before every filter regeneration event, eventually taking into account the remaining evaporation time.

In order to estimate the HydroCarbons (HC) Evaporation Time after the end of a filter regeneration event, the following equation may be used for this purpose: New Evaporation Time=Old Evaporation Time−Evaporation Time Elapsed+Evaporation Time Setpoint. At the start of the estimation, namely after the first regeneration process has ended, the value of Old Evaporation Time is necessarily zero since no previous evaporation has occurred; the same is true for the Evaporation Time Elapsed value. Therefore the value of New Evaporation Time at this first evaporation event is set equal to the Evaporation Time Setpoint. The second and further iterations of the above equation will take into account the value of the evaporation time elapsed in the previous evaporation event in order to calculate the evaporation time for the current event.

The variable New Evaporation Time will act as the saturation for all the following evaporation phases. If the mission profile changes, also the Evaporation Time Setpoint is changed accordingly using the correct preset value for that mission profile. The variable Evaporation Rate indicates the rate of change of the oil viscosity increase during the evaporation time; this rate depends on the Mission Profile since the Fuel Injections pattern depends on both the engine working point and on external conditions, thus in the present method the Evaporation Rate is correlated to the specific Mission Profile. Such variable is also useful for calibration purposes.

The variable Dilution Rate indicates the rate of change of the oil viscosity decrease during the filter regeneration; this rate depends on the Mission Profile, since the Post Fuel Injections depend on both the engine working point and on external conditions, thus in the present method the Dilution Rate is correlated to the specific Mission Profile. Such variable is also useful for calibration purposes.

Figure 4:
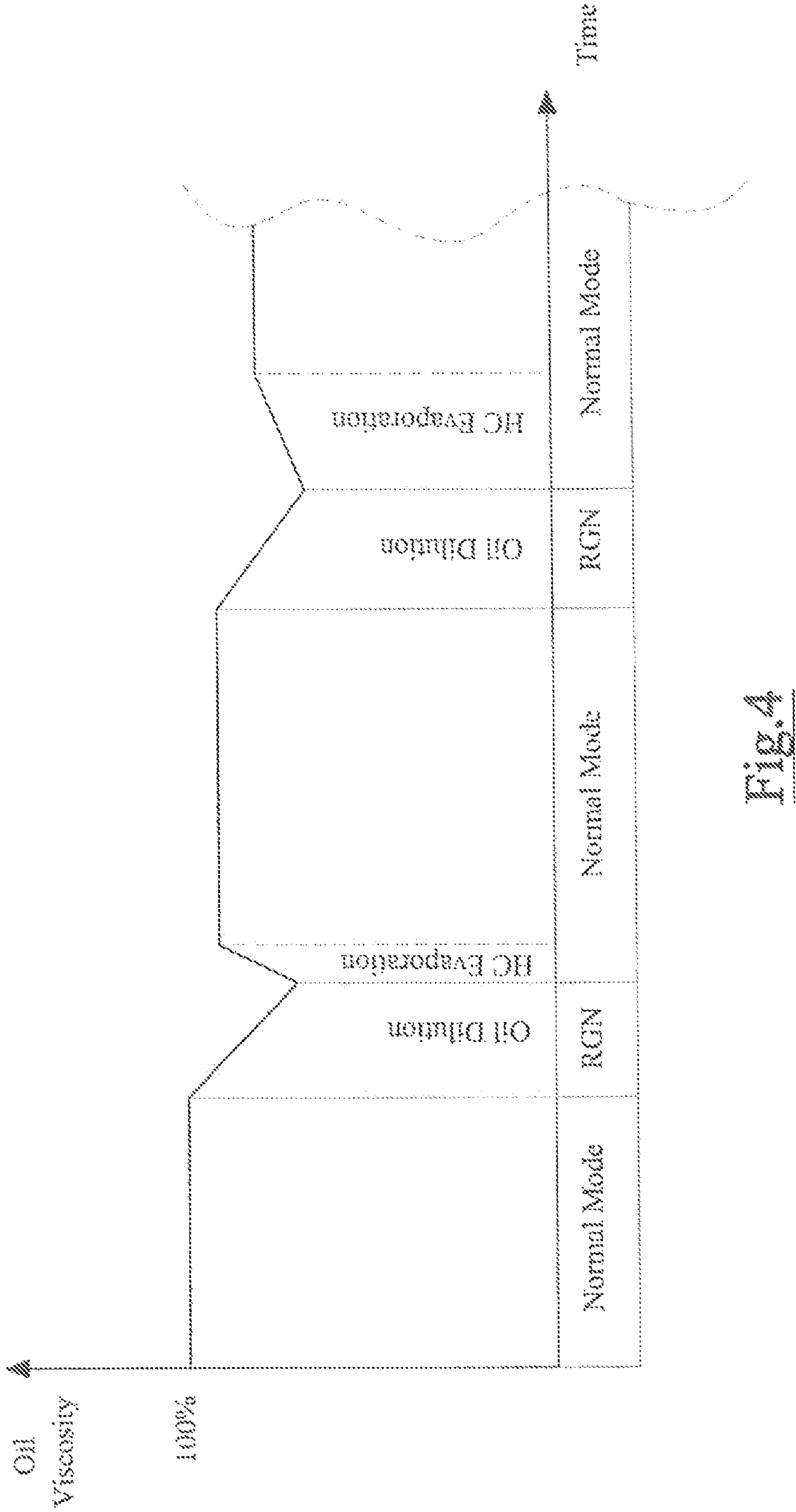
FIG. 4 is a graph depicting an example of the behavior of an estimation of oil viscosity over time according to an embodiment during two subsequent oil dilution-HC evaporation cycles, each of them performed in a single Mission Profile.

An embodiment of the method will now be described taking into account the hypothesis of a single Mission Profile, as exemplified in FIG. 4. In the example, starting from an Oil Viscosity of approximately 100%, as long as the engine operates normally, namely without performing a filter regeneration, there is no change in oil viscosity. As soon as a first filter regeneration process starts, oil viscosity starts to decrease, since Post Injection fuel hits and wets the walls of the combustion chamber and it is adsorbed to the oil, causing a decrease in oil viscosity. Since the decrease in viscosity depends on the specific mission profile, the method estimates such decrease over time using a specific value for the Dilution Rate variable for that mission profile. Accordingly, the behavior of the estimation of oil viscosity over time in FIG. 4 shows a decrease in oil viscosity for the time employed in such regeneration process.

When the regeneration process stops, oil viscosity increases because, during normal operation of the engine, some of the fuel hydrocarbons inside the oil evaporates (HC Evaporation). However, this evaporation stops at a certain point in time when saturation occurs. When the evaporation stops, oil viscosity does not normally reach 100% therefore, during the remaining normal mode engine working period, no change in the viscosity is estimated. The method can continue considering further regeneration processes and the consequent phases of oil dilution and HC evaporation.

It must be noted that the above described method mirrors effectively the phenomena that influence oil viscosity. In fact, as can be seen from FIG. 2, a known method (whose behavior is indicated with a dotted line) does not take into account the history of the oil and therefore does not adjust evaporation time accordingly.

Figure 2:
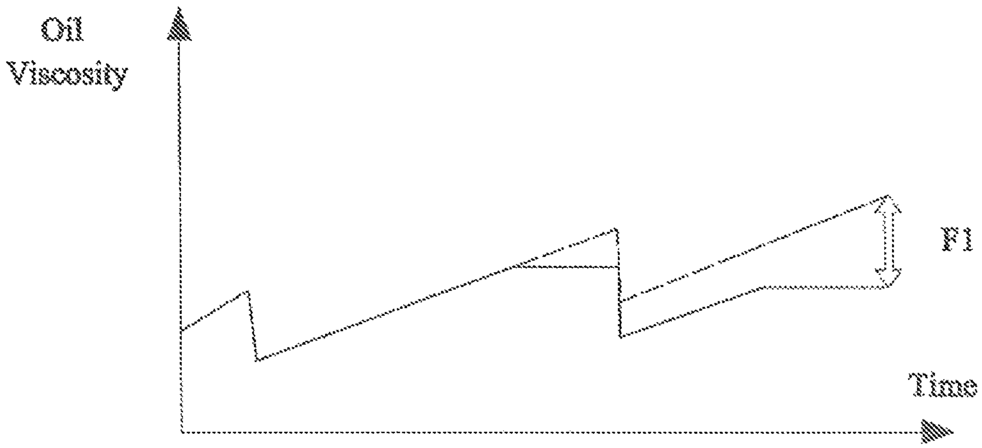
FIG. 2 is a graph comparing experimental data of oil dilution over time with the estimations given by a known method and by the method herein disclosed.

This has the effect that after only two evaporation phases an error estimation can reach 6% or more, with respect to the method of this disclosure, as shown by the arrow F1 in FIG. 2.

After less than twenty Evaporation Phases, a 60% over-estimation error on the oil may occur leading to undesirable conditions for the engine. On the contrary, with increased frequency of the regeneration events, the method herein described keeps track of the history of the oil, adjusting the evaporation time accordingly.

Figure 5:
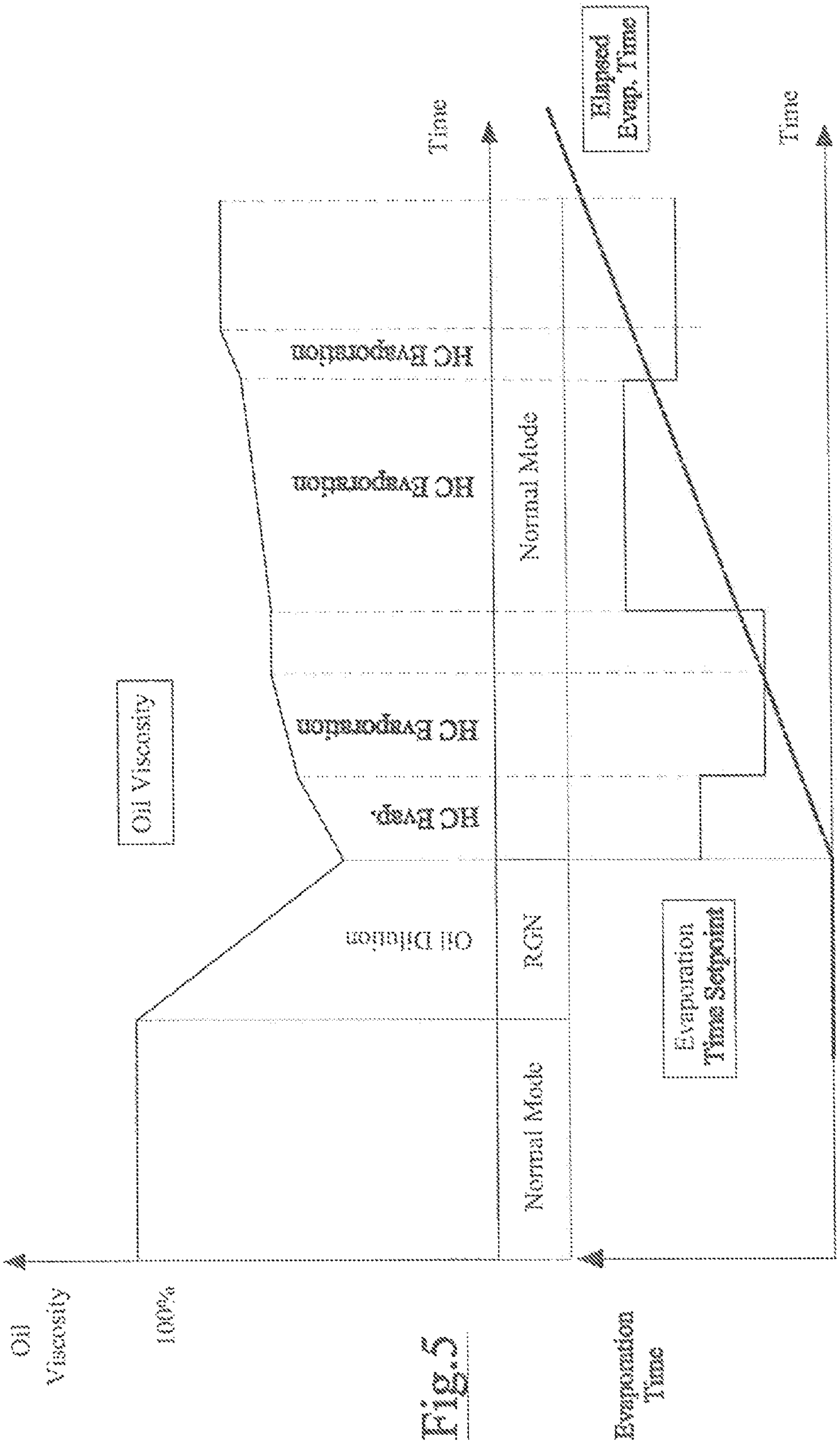
FIG. 5 is a graph depicting an example of the behavior of estimation of oil viscosity over time according to a further embodiment during use of a vehicle that is subjected to multiple different Mission Profiles over time, during the HC evaporation phase.

A further embodiment of the method will now be described taking into account the hypothesis of different Mission Profiles occurring during the life of the engine, as exemplified in FIG. 5. Starting from an Oil Viscosity of 100%, as long as the engine operates normally, namely without performing a filter regeneration, there is no change in oil viscosity. As soon as a first filter regeneration process starts, oil viscosity starts to decrease. Since different mission profiles are taken into account, the method provides for an Evaporation Time Setpoint value for each of them, as also exemplified in the lower portion of FIG. 5.

If, during an evaporation phase, the mission profile changes (for example from HIGHWAY HIGH to HIGHWAY LOW), a different Evaporation Time Setpoint value is selected corresponding to said Mission Profile. Also a different Evaporation Rate is selected corresponding to the same Mission Profile. Furthermore, when evaporation is over, if during normal operation of the engine, the engine experiences a still different Mission Profile, a still different Evaporation Time Setpoint value is selected. Also a still different Evaporation Rate is selected corresponding to the same Mission Profile. Also, if a further filter regeneration occurs a corresponding Dilution Rate is selected corresponding to the same Mission Profile. These operations can continue during use of the vehicle keeping track of the history of the oil and arriving at a reliable estimation of oil viscosity.

Furthermore, according to another embodiment of the invention, using the output of the estimated oil viscosity it is possible to implement various actions in order to reduce or even eliminate the risk of engine 10 damage due to overestimated oil life, for example in case of particular conditions such as a high number of interrupted DPF regenerations or an increased frequency of the DPF regenerations.

For these aims, a first minimum threshold oil viscosity value may be set and if the estimated oil viscosity values drops below the first minimum threshold value, a warning signal may be generated. Such warning signal may be, for example, a light or sound signal to warn the driver that the engine 10 needs an oil change. Furthermore, if the oil viscosity drops below the first predetermined minimum threshold value or, alternatively, if it drops below a second predetermined minimum threshold value that is lower than the first predetermined minimum threshold value engine operation is changed to ensure that the engine 10 is not damaged. In this case, for example, the ECU may select an engine operating mode in which a maximum value of torque is generated by the engine 10.

Advantageously the method described achieving a substantial improvement in oil viscosity estimation leads to a engine durability increase, an increase in general engine system robustness and to warranty cost savings.

While at least one exemplary embodiment has been presented in the foregoing summary and detailed description, it should be appreciated that a vast number of variations exist. It should also be appreciated that the exemplary embodiment or exemplary embodiments are only examples, and are not intended to limit the scope, applicability, or configuration in any way. Rather, the foregoing summary and detailed description will provide those skilled in the art with a convenient road map for implementing at least one exemplary embodiment, it being understood that various changes may be made in the function and arrangement of elements described in an exemplary embodiment without departing from the scope as set forth in the appended claims and their legal equivalents.

What is claimed is:

1. A method for a estimation of oil viscosity in an internal combustion engine, the internal combustion engine subjected to fuel post injections to activate a regeneration process of a particulate filter and to a fuel hydrocarbon evaporation events affecting oil viscosity, comprising:

determining if the particulate filter is subjected to the regeneration process, and if the particulate filter is subjected to the regeneration process:

calculating an oil viscosity decrease during the regeneration process as a function of an oil dilution rate; and calculating an oil viscosity increase after the regeneration process as a function of an hydrocarbon evaporation rate and of a time during which fuel hydrocarbon evaporation takes place, wherein the time is a function of time spent evaporating one or more kinds of fuel hydrocarbons from engine oil in a previous fuel hydrocarbon evaporation event; and wherein a different hydrocarbon evaporation rate is set for each kind of fuel hydrocarbon following a regeneration process based upon a specific mission profile of the internal combustion engine.

2. The method according to claim 1, wherein the oil viscosity is incremented until the time spent in evaporating fuel hydrocarbons from engine oil reaches a set point value.

3. The method according to claim 2, wherein different set point values for the time spent evaporating fuel hydrocarbons are preset for each mission profile of the internal combustion engine.

4. The method according to claim 1, wherein a different oil dilution rate is set for each regeneration process on a basis of a specific mission profile in which the internal combustion engine is operating.

5. A method for operating an internal combustion engine, the internal combustion engine subjected to fuel post injections to activate a regeneration process of a particulate filter and to fuel hydrocarbons (HC) evaporation events affecting an oil viscosity, comprising:

determining if the particulate filter is subjected to the regeneration process and if the particulate filter is subjected to the regeneration process;

calculating an oil viscosity decrease during the regeneration process as a function of an oil dilution rate;

calculating an oil viscosity increase after the regeneration process as a function of a hydrocarbon evaporation rate and of a time during which fuel hydrocarbon evaporation takes place, wherein the time is a function of time spent evaporating one or more kinds of fuel hydrocarbons from engine oil in a previous fuel hydrocarbons evaporation event;

wherein a different hydrocarbon evaporation rate is set for each kind of fuel hydrocarbon following a regeneration process based upon a specific mission profile of the internal combustion engine; and generating a warning signal if the oil viscosity value drops below a first predetermined minimum threshold value.

6. The method according to claim 5, wherein if the oil viscosity value drops below the first predetermined minimum threshold value the internal combustion engine is operated in an operating mode in which torque generated by the internal combustion engine may not exceed a preset maximum threshold torque value.

7. A computer readable medium embodying a computer program product, the computer program product comprising:

a estimation program for an estimation of oil viscosity in an internal combustion engine, the internal combustion engine subjected to fuel post injections to activate a regeneration process of a particulate filter and to a fuel hydrocarbon evaporation events affecting oil viscosity, the estimation program configured to:

determine if the particulate filter is subjected to the regeneration process, and if the particulate filter is subjected to the regeneration process:

calculate an oil viscosity decrease during the regeneration process as a function of an oil dilution rate; and calculate an oil viscosity increase after the regeneration process as a function of an hydrocarbon evaporation rate and of a time during which fuel hydrocarbon evaporation takes place, wherein the time is a function of time spent in evaporating one or more kinds of fuel hydrocarbons from engine oil in a previous fuel hydrocarbon evaporation event; and wherein a different hydrocarbon evaporation rate is set for each kind of fuel hydrocarbon following a regeneration process based upon a specific mission profile of the internal combustion engine.

8. The computer readable medium embodying the computer program product according to claim 7, wherein the oil viscosity is incremented until the time spent evaporating fuel hydrocarbons from engine oil reaches a set point value.

9. The computer readable medium embodying the computer program product according to claim 8, wherein different set point values for the time spent in evaporating fuel hydrocarbons are preset for each mission profile of the internal combustion engine.

10. The computer readable medium embodying the computer program product according to claim 7, wherein a different oil dilution rate is set for each regeneration process on a basis of a specific mission profile in which the internal combustion engine is operating.

11. A computer readable medium embodying a computer program product, the computer program product comprising:

an estimation program for operating an internal combustion engine, the internal combustion engine subjected to fuel post injections to activate a regeneration process of a particulate filter and to fuel hydrocarbons (HC) evaporation events affecting an oil viscosity, the estimation program configured to:

determine if the particulate filter is subjected to the regeneration process and if the particulate filter is subjected to the regeneration process;

calculate an oil viscosity decrease during the regeneration process as a function of an oil dilution rate;

calculate an oil viscosity increase after the regeneration process as a function of a hydrocarbon evaporation rate and of a time during which fuel hydrocarbon evaporation takes place;

wherein the time is a function of time spent in evaporating one or more kinds of fuel hydrocarbons from engine oil in a previous fuel hydrocarbons evaporation event (evaporation time elapsed);

wherein a different hydrocarbon evaporation rate is set for each different kind of fuel hydrocarbon and each hydrocarbon evaporation rate is a function of a specific mission profile of the internal combustion engine; and generate a warning signal if the oil viscosity value drops below a first predetermined minimum threshold value.

12. The computer readable medium embodying the computer program product according to claim 11, wherein if the oil viscosity value drops below the first predetermined minimum threshold value the internal combustion engine is operated in an operating mode in which torque generated by the internal combustion engine may not exceed a preset maximum threshold torque value.

* * * * *